United States Patent [19]

Karami et al.

[11] Patent Number: 4,573,989

[45] Date of Patent: Mar. 4, 1986

[54] DISPOSABLE DIAPER AND METHOD OF MANUFACTURE

[75] Inventors: Hamzeh Karami, Embourg; Myriam Delvaux, Hannut, both of Belgium

[73] Assignee: Colgate-Palmolive Company, New York, N.Y.

[21] Appl. No.: 449,364

[22] Filed: Dec. 13, 1982

[51] Int. Cl.$^4$ .............................................. A61F 13/16
[52] U.S. Cl. .................................... 604/381; 604/365
[58] Field of Search .............. 604/381, 379, 365, 366, 604/367, 374, 375

[56] References Cited

U.S. PATENT DOCUMENTS

| | | | |
|---|---|---|---|
| 3,903,889 | 9/1975 | Torr | 604/381 |
| 3,996,936 | 12/1976 | Widlund et al. | 604/381 |
| 4,044,768 | 8/1977 | Mesek et al. | 604/381 |
| 4,102,340 | 7/1978 | Mesek et al. | 604/381 |
| 4,176,667 | 12/1979 | Herring | 604/365 |
| 4,260,443 | 4/1981 | Lindsay et al. | 604/365 |

*Primary Examiner*—John D. Yasko
*Attorney, Agent, or Firm*—Herbert S. Sylvester; Murray M. Grill; Norman Blumenkopf

[57] ABSTRACT

A disposable diaper comprising an absorbent pad or dual absorbent pads positioned between a top sheet and a waterproof backing sheet without the presence of wadding sheets to increase the suppleness of the diaper. A binder is sprayed between said pad or the lower of the dual pads and the backing sheet, the binder penetrating the material of the pad to stick the pad to the backing sheet to render the pad highly tear resistant.

3 Claims, 2 Drawing Figures

U.S. Patent    Mar. 4, 1986    4,573,989

DISPOSABLE DIAPER AND METHOD OF MANUFACTURE

BACKGROUND OF THE INVENTION

1. Field of the Invention

This invention relates to disposable diapers which are particularly resistant to tearing and more supple.

2. Description of the Prior Art

Disposable diapers as heretofore produced employ an absorbent pad assembly positioned between a top sheet and a backing sheet. The absorbent pad assembly included wadding sheets at the top and bottom thereof. To stabilize the absorbent pad assembly, the cold or hot melt adhesives were employed between the wadding sheets of the absorbent pad assembly and the top sheet or backing sheet or both. The use of the wadding sheets caused lessened suppleness of the diaper and the use of adhesives further lessened the suppleness of the diaper.

The absorbent pad assembly usually employed one or more pads of wood fluff which was relatively loose and almost non-resistant to tearing.

Binders have been used in the past to stabilize the absorbent pad to the wadding sheets whereby suppleness is further lessened.

SUMMARY OF THE INVENTION

The present invention has for its object to overcome the disadvantages of prior art disposable diapers by increasing the suppleness of the diaper while rendering the diaper resistant to tearing.

The foregoing is accomplished according to the invention by positioning an absorbent pad or dual pads between a top sheet and a backing sheet of waterproof polyethylene or polypropylene film. A binder is sprayed between said pad or the lower of the dual pads and said backing sheet and either on the pad or backing sheet or both to stabilize the pad to the backing sheet. The binder penetrates the absorbent material of the pad to stick the absorbent material to the backing sheet.

DETAILED DESCRIPTION OF THE INVENTION

Figure 1:
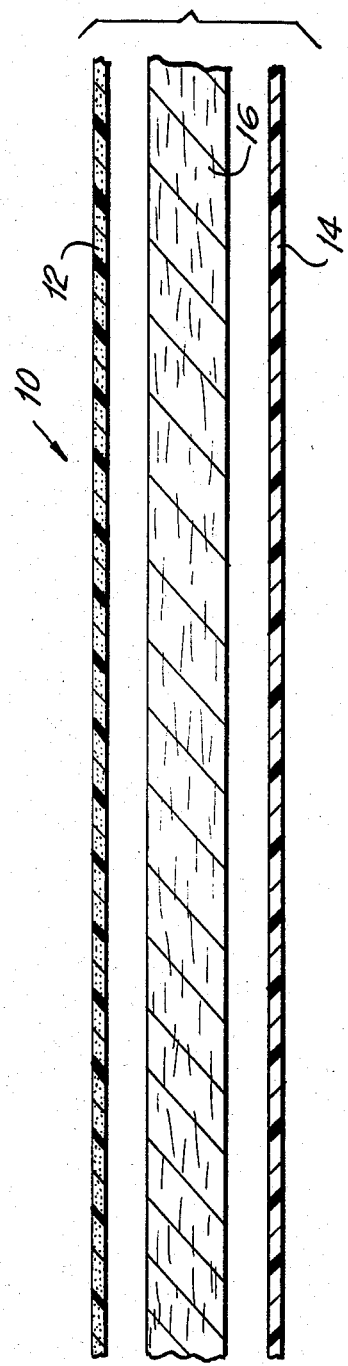
FIG. 1 is an exploded sectional view of a disposable diaper constructed in accordance with the invention; and, FIG. 2 is a view similar to FIG. 1 showing a modified embodiment employing a dual pad assembly.

With initial reference to the embodiment of the invention shown in FIG. 1, reference numeral 10 generally designates a diaper made in accordance with the concepts of the invention. The diaper includes a top sheet 12, a backing sheet 14, and an absorbent pad positioned between the top sheet 12 and the backing sheet 14. The top sheet 12 and backing sheet 14 are bonded to each other substantially around the periphery thereof by conventional bonding means, which may include adhesive material, thermal or sonic bonding, or other conventional means.

The top sheet 12 may be made of a hydrophobic material, such as non-woven fibers of polyethylene or polypropylene or a combination of both.

The backing sheet 14 is of a waterproof material, such as a film of polyethylene or polypropylene.

The absorbent pad 16 is characterized by the absence of wadding sheets rendering the diaper distinctly more supple. The pad may be made of wood fluff with or without application of super-absorbent polymers known to the art. The wood fluff is a loosely disposed material essentially more resistant to tearing.

A binder solution is sprayed between the backing sheet 14 and the underside of the pad 16. The spray may be directed onto the backing sheet 14, the underside of the absorbent pad 16 or both and penetrates the absorbent pad 16 stabilizing the pad 16 and sticking the wood fluff even at the upper portions of said pad 16 either directly or indirectly through other fibers of the wood fluff to the backing sheet. This renders the diaper resistant to tearing.

Of course, the binder spray can be applied preferably to the whole pad area or may be partially sprayed on a selected part of the pad 16 only.

In the making of the diaper, the binder spray can be continuous or intermittent and may contain a surfactant to increase fiber wetability of the absorbent pad 16.

Figure 2:
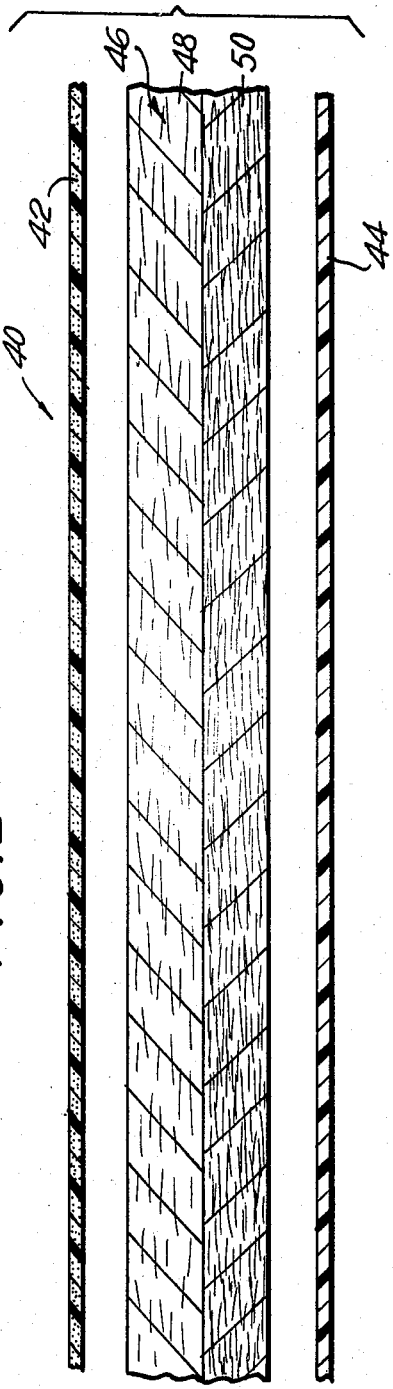

Referring now to the embodiment of the invention shown in FIG. 2, herein the diaper is generally indicated by reference numeral 40. The top sheet 42 and the backing sheet 44 are the same as the top sheet 12 and backing sheet 14 shown in FIG. 1. In lieu of a single absorbent pad, a dual pad assembly 46 is employed and is positioned between the top sheet 42 and the backing sheet 44. The dual pad assembly includes an upper pad 48 and a lower pad 50 and is characterized by the absence of wadding sheets, thereby rendering the diaper 40 more supple than prior art diapers employing wadding sheets.

The pads 48 and 50 may be of the same or different sizes and may be of different materials, or the same materials, and may be the same or of different densities and thicknesses. The pads 48 and 50 are preferably formed of wood fluff, which can be optionally treated with a super-absorbent polymer.

A spray of liquid binder is applied between the pad 50 and the backing sheet 44. The spray may be directed on the backing sheet 44 or on the pad 50 or both and the spray penetrates the absorbent wood fluff material to stick either directly or indirectly the fibers of the wood fluff directly to the backing sheet to stabilize the entire pad 50. This eliminates the necessity for adhesives which might otherwise be used which would render the diaper less supple. The binder material serves to render the diaper resistant to tearing. A surfactant can be used in connection with the binder to increase the wetability of the fibers of the pad.

It is to be understood that this construction may be used in diapers of any shape or style such as flat rectangular diapers, diapers of box-pleated configuration or contoured diapers and is equally applicable to non-elasticized diaper and elasticized diapers having elasticized crotch and/or waist members.

What is claimed is:

1. A disposable diaper comprising an absorbent pad positioned between a top sheet and a waterproof backing sheet, said absorbent pad being characterized by the absence of wadding sheets to improve suppleness of said diaper, and a liquid binder sprayed on said backing sheet between said absorbent pad and said backing sheet to stabilize said pad to said backing sheet.

2. A disposable diaper comprising an absorbent dual pad assembly positioned between a top sheet and a waterproof backing sheet of polyethylene or polypropylene film, said pad assembly being characterized by the absence of wadding sheets to increase the suppleness of said diaper, said absorbent pad assembly including an upper and lower pad, and a binder on said backing sheet between said lower pad and said backing sheet to stabilize said lower pad to said backing sheet.

3. A method of making a disposable diaper comprising the steps of positioning an absorbent pad assembly between a top sheet and a waterproof backing sheet without the use of wadding sheets, and then spraying a liquid binder between said absorbent pad and said backing sheet and on said backing sheet so that said binder stabilizes said pad to said backing sheet.

* * * * *